United States Patent
Yada et al.

(10) Patent No.: US 7,037,411 B2
(45) Date of Patent: May 2, 2006

(54) APPARATUS AND METHOD FOR HANDLING EASILY POLYMERIZABLE SUBSTANCE, APPARATUS FOR EXTRACTING LIQUID FROM APPARATUS UNDER REDUCED PRESSURE, AND PROCESS FOR PRODUCING EASILY POLYMERIZABLE SUBSTANCE

(75) Inventors: Shuhei Yada, Yokkaichi (JP); Yasushi Ogawa, Yokkaichi (JP); Hirochika Hosaka, Yokkaichi (JP); Yoshiro Suzuki, Yokkaichi (JP); Mitsuo Nakamura, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/871,577

(22) Filed: Jun. 21, 2004

(65) Prior Publication Data

US 2004/0226812 A1 Nov. 18, 2004

Related U.S. Application Data

(63) Continuation of application No. PCT/JP02/13373, filed on Dec. 20, 2002.

(30) Foreign Application Priority Data

Dec. 21, 2001 (JP) ............... 2001-390046
Jan. 16, 2002 (JP) ............... 2002-007449

(51) Int. Cl.
  *B01D 3/10* (2006.01)
  *B01D 35/02* (2006.01)
  *C02F 51/44* (2006.01)
  *F04B 39/16* (2006.01)

(52) U.S. Cl. ............... 202/205; 202/160; 137/565.23; 137/625.28; 210/295; 210/428; 562/600

(58) Field of Classification Search ............... 202/160, 202/205; 210/295, 428; 137/565.23, 625.28; 562/600; 203/1, 2, 91, 100
See application file for complete search history.

(56) References Cited

U.S. PATENT DOCUMENTS 3,797,744 A * 3/1974 Smith .................. 239/172
5,148,945 A * 9/1992 Geatz .................. 222/1

(Continued)

FOREIGN PATENT DOCUMENTS

JP 8-24528 1/1996

(Continued)

OTHER PUBLICATIONS

English Translations of Japan 2000-336162 and JApan 8-24528.*

*Primary Examiner*—Virginia Manoharan
(74) *Attorney, Agent, or Firm*—Wenderoth, Lind & Ponack, L.L.P.

(57) ABSTRACT

In an apparatus capable of distilling and refining an easily polymerizable substance, piping is performed so that when a strainer in action is switched to a backup strainer, the strainer can be switched after removing air in the backup strainer to replace air in the backup strainer with a discharge liquid of a pump. According to the apparatus, switching the strainers installed on an upstream side of the pump for extracting a liquid of a vacuum distillation column, which distills and refines the easily polymerizable substance, can be performed with no trouble during operation of the distillation column. When the apparatus includes a device for measuring a differential pressure between an upstream side and a downstream side of the strainer in action, two or more strainers installed in parallel can be switched at proper times and the easily polymerizable substance can be produced efficiently.

6 Claims, 4 Drawing Sheets

U.S. PATENT DOCUMENTS

| | | | |
|---|---|---|---|
| 5,417,346 A | * | 5/1995 | Ferri et al. .................... 222/61 |
| 6,676,808 B1 | * | 1/2004 | Hamamoto et al. ............ 203/8 |
| 6,833,056 B1 | * | 12/2004 | Kamiya et al. ............. 202/155 |

FOREIGN PATENT DOCUMENTS

| | | |
|---|---|---|
| JP | 2000-336162 | 12/2000 |

* cited by examiner

APPARATUS AND METHOD FOR HANDLING EASILY POLYMERIZABLE SUBSTANCE, APPARATUS FOR EXTRACTING LIQUID FROM APPARATUS UNDER REDUCED PRESSURE, AND PROCESS FOR PRODUCING EASILY POLYMERIZABLE SUBSTANCE

This is a Rule 1.53(b) Continuation of PCT/JP02/13373, filed Dec. 20, 2002.

TECHNICAL FIELD

The present invention relates to an apparatus for extracting a liquid, particularly a liquid potentially containing solids, from an apparatus under reduced pressure, and to a process for producing an easily polymerizable substance which comprises switching two or more strainers parallelly installed in a liquid extraction pipe at proper times, wherein the liquid extraction pipe is connected to a pump for transferring an outlet liquid from a treating column for handling the easily polymerizable substance.

BACKGROUND ART

When distilling and refining easily polymerizable substances, for example, acrylic acid and methacrylic acid or their esters, distillation is performed with addition of polymerization inhibitors and under reduced pressure in order to prevent polymerization from occurring. However, it is impossible to completely prevent polymerization and it is inevitable that some polymerization occurs. In particular, for example, a drastic change in conditions under which a distillation apparatus is operated for any reason may result in an abrupt progress in polymerization. Therefore, some polymerisate may exist in distillation residue drawn out from a bottom of the distillation apparatus and polymerisate may also be contained in condensate in a reflux tank at a top of the apparatus.

Extracting distillation residues at a bottom of the column to an exterior, extracting condensate in the reflux tank at a top of the column to the exterior, or refluxing the condensate to a distillation column needs aid of a pump. However, direct supply of a liquid that contains solids such as a polymerisate may cause solids to be attached to a casing part of the pump or enter into a mechanical seal part of the pump. Once such a phenomenon occurs, flow is stagnated at that portion, so that polymerization of a polymerizable substance in the distillation residue proceeds, thus causing a serious problem in operation of the pump, and ultimately it becomes inevitable to stop the operation of the pump.

Further, it is possible that solids that passed the pump may cause clogging of a flow meter and control valve provided on a discharge side of the pump. Therefore, a strainer is provided usually on an upstream side of the pump in order to avoid feeding of solids to the pump. To allow for continued operation of the distillation column even when the strainer is clogged with solids, two or more strainers are provided in parallel. In a case where one strainer which is in operation is clogged, a backup strainer provided in parallel can be immediately brought into operation by switching valves.

However, in general, switching a strainer of a pump for extracting a liquid from a vacuum distillation apparatus to a backup strainer tends to cause an abnormal operation of the pump. Also, in a case of distillation and refining of a polymerizable substance, switching strainers of a pump for extracting a condensate from a reflux tank may result in production of a polymerisate in the condensate in the reflux tank. Also in a case of switching the strainers of a pump for extracting distillation residue from a bottom of a column, production of polymerisate in the column may increase.

The inventors of the present invention have studied a cause therefor and as a result, they have found that such is attributable to air contained in the backup strainer. That is, a strainer clogged with solids becomes a backup strainer to be opened and cleaned. These operations are performed in air and hence atmospheric air is present in the backup strainer. Accordingly, operation of the backup strainer will result in back flow of inside air to an upstream side to flow into the apparatus under reduced pressure, or flow into the pump located downstream, or further into an apparatus to which a discharge liquid of the pump flows. As a result, operation of the pump is disturbed and the operation of the pump must be stopped, as the case may be.

Further, this disturbed operation of the pump or flowed in air will disturb flow of steam and liquid within the distillation apparatus, with a result that polymerization of a polymerizable substance is promoted. That is, although a polymerization inhibitor is fed to a condenser at the top of the column to prevent the condensate from polymerizing when distilling and refining a polymerizable substance, it is conceivable that disturbed flow of steam in the condenser will produce a condensate in which concentration of the polymerization inhibitor is locally reduced, which triggers polymerization.

Further, back flow into the distillation column of the air in the backup strainer of a pump for extracting distillation residues from the bottom of a column will disturb the flow of the steam and liquid in the column, causing local stagnation of the liquid or local concentration reduction of the polymerization inhibitor to promote polymerization.

In a process where acrylic acid, methacrylic acid, and esters thereof, which are typically easily polymerizable substances, are produced by catalytic gas phase oxidation, it is important to stabilize operational conditions of respective unit operation apparatuses used in unit operations such as separation or purification of acrylic acid, methacrylic acid and esters thereof, from a viewpoint of stable production of these substances, which are easily polymerizable substances, in order to suppress formation of polymerisate that will frequently occur during the operation.

Since these substances are easily polymerizable substances, polymerisate is generated inside of a plant in spite of use of a polymerization inhibitor or a polymerization retardant. For example, polymerisate is produced inside each distillation column and condenser that constitute a process, and the polymerisate is accumulated inside of the distillation column, or a part of or all of the polymerisate falls to the bottom of the column, or clogs the condenser, or falls to the reflux tank or the pump connected to the reflux tank through a line.

To remove the polymerisate, for example, a strainer installed on a feed side of a pump for transferring a column bottom liquid that transfers the column bottom liquid to a downstream appliance is provided for purposes of protecting the pump, preventing polymerization solids from being fed to the appliance downstream of the pump, and the like. Further, since continuous operation is intended, two or more strainers parallelly installed (one strainer being in action and other strainer(s) being in a standby state) are provided.

In a case where an easily polymerizable substance is produced, although polymerisate generated can be collected by the strainer and removed from the process thereby, times of switching to the strainer provided as a backup cannot be judged since a state of the polymerisate being collected during the operation of the strainer cannot be grasped. That is, an increased amount of collection will cause clogging of the strainer with collected polymerizate, thus generating cavitation in the pump connected to the strainer. This causes abnormality of pump operation, which in turn leads to disturbed operational conditions (for example, variation in pressure, variation in flow rate, and variation in temperature) in appliances installed on upstream and downstream sides of the pump, thereby generating polymerisate in appliances to stop operation of the appliances or the plant in its entirety.

For this reason, the strainers are frequently switched to cope with the aforementioned problems; however, this incurs a labor load to an operator who operates, and in a case where a substance to be handled is a dangerous substance, toxic substance, or the like, utmost care must be taken and the operator is put under a great psychological burden.

Easily polymerizable substances, particularly acrylic acid, methacrylic acid, and esters thereof have this tendency to such a significant extent. And in an industrial production plant, a countermeasure is demanded to reduce a burden on the operator and avoid a situation where the operation has to be stopped.

SUMMARY OF THE INVENTION

An object of the present invention is to provide an apparatus for extracting a liquid, and an apparatus and method for handling an easily polymerizable substance, in which problems of operation caused by air contained in a backup strainer can be avoided.

Further, another object of the present invention is to switch two or more strainers at proper times, wherein the strainers are parallelly installed in a liquid extraction pipe for transferring an outlet liquid of a treating column from the treating column for handling the easily polymerizable substance to the pump for transferring the outlet liquid, in a process for producing an easily polymerizable substance and an apparatus and method for handling an easily polymerizable substance.

The apparatus and method for handling an easily polymerizable substance according to the present invention is as follows.

(1) An apparatus for handling an easily polymerizable substance, comprising: a decompressor for handling the easily polymerizable substance under reduced pressure; a liquid extraction pipe having an upstream end that opens in the decompressor; a pump provided in a middle of the liquid extraction pipe; a plurality of strainers connected parallel to one another to the liquid extraction pipe on an upstream side of the pump; and valves provided on an upstream side and downstream side of each strainer, wherein the apparatus comprises at least one of constructions (A) and (B) below:

(A) an exhaust device for exhausting air in a part sandwiched between the valves provided on the upstream side and downstream side of each strainer, and a branch pipe that connects the part sandwiched between the valves provided on the upstream side and downstream side of each strainer and the liquid extraction pipe on the downstream side of the pump; and (B) a device for measuring a differential pressure between a pressure in the liquid extraction pipe on the upstream side of each strainer and a pressure in the liquid extraction pipe on the downstream side of each strainer.

(2) The apparatus according to (1), wherein the exhaust device is configured such that when a liquid is introduced from the branch pipe to the part sandwiched between the valves provided on the upstream side and downstream side of each strainer, the liquid expels air in the part.

(3) The apparatus according to (1) or (2), wherein the decompressor for handling the easily polymerizable substance under reduced pressure is an apparatus for distilling an easily polymerizable polymer selected from the group consisting of acrylic acid, methacrylic acid, and esters thereof under reduced pressure.

(4) A method for handling an easily polymerizable substance using the apparatus according to any one of (1) to (3), comprising: using the strainers one by one; determining a time for switching the strainers to measure a difference between a pressure in the liquid extraction pipe on an upstream side of the strainer being used and a pressure in the liquid extraction pipe on a downstream side of the strainer being used; and switching the strainer being used to another one of the strainers.

(5) The method according to (4), further comprising: discharging air in a part sandwiched between valves provided on the upstream side and downstream side of the another strainer; feeding a discharge liquid of the pump from the branch pipe to the part; and switching the strainer being used to another strainer after replacing air in the part with discharge liquid.

The apparatus for extracting a liquid from an apparatus under reduced pressure according to the present invention is as follows.

(6) An apparatus for extracting a liquid from an apparatus under reduced pressure, comprising: a liquid extraction pipe for transferring a liquid under reduced pressure contained in an apparatus under reduced pressure, having an upstream end that opens in the apparatus under reduced pressure, and having a pump in a middle of the pipe; strainers connected in parallel to the liquid extraction pipe on an upstream side of the pump; valves provided on an upstream side and downstream side of each strainer; an exhaust device for exhausting air in a part sandwiched between the valves; and a branch pipe that connects a part sandwiched between the valves provided on the upstream side and downstream side of each strainer and the liquid extraction pipe on a downstream of the pump.

(7) The apparatus according to (6), wherein the exhaust device is configured such that when a liquid is introduced from the branch pipe to the part sandwiched between the valves provided on the upstream side and downstream side of each strainer, the liquid expels air from the part.

(8) The apparatus according to (6) or (7), wherein the apparatus under reduced pressure is a vacuum distillation apparatus for an easily polymerizable substance selected from the group consisting of acrylic acid, methacrylic acid, and esters thereof.

In the apparatus for extracting a liquid from an apparatus under reduced pressure according to the present invention, switching to a backup strainer is performed as follows. First, discharged liquid from the pump is introduced to the backup strainer through a branch pipe by switching valves, air in the backup strainer is replaced by the discharged liquid, and then the backup strainer is brought into action. Therefore, a disturbed operation due to air in the backup strainer can be avoided.

Further, the inventors of the present invention have made diligent study on the aforementioned problem, and as a result they have found that proper times for switching strainers can be determined by measuring a differential pressure between a pressure in the liquid extraction pipe on the upstream side of the strainer being used and a pressure in the liquid extraction pipe on the downstream side of the strainer being used in order to grasp a condition of the strainer. Thus, the present invention is accomplished.

That is, a process for producing an easily polymerizable substance according to the present invention is as follows.

(9) A process for producing an easily polymerizable substance using a treating apparatus having one or two, or more, treating columns for treating the easily polymerizable substance, a pump provided in each treating column for transferring an outlet liquid of the treating column, and two or more strainers installed parallelly in a liquid extraction pipe connecting the treating column and the pump, wherein the process comprises:

using the two or more strainers one by one in each treating column; determining a time of switching the strainers to measure a difference between a pressure in the liquid extraction pipe on an upstream side of the strainer being used and a pressure in the liquid extraction pipe on a downstream side of the strainer being used; and switching the strainer being used to another strainer out of the two or more strainers.

(10) The process according to (9), wherein a differential pressure of the strainer being used is continuously measured.

(11) The process according to (9), wherein extraction nozzles for connecting a detection end for measuring pressure are installed to a top of the liquid extraction pipe of the strainer being used.

(12) The process according to any one of (9) to (11), in which the easily polymerizable substance is selected from the group consisting of acrylic acid, methacrylic acid, and esters thereof.

(13) The process according to any one of (9) to (12), wherein the treating apparatus comprises the treating column(s) selected from any one of a distillation column, an evaporation column, a reflux tank, an extraction column, an absorption column, a high boiling point decomposition reactor, an esterification reactor, a heat exchanger or combinations thereof.

<An Apparatus of the Present Invention for Extracting a Liquid from an Apparatus Under Reduced Pressure>

The present invention will be described in more detail with reference to the attached drawings. FIG. 1 shows an example of an apparatus for extracting a liquid according to the present invention.

Reference numerals 1 and 2 stand for strainers. The strainers may be those employed in general chemical apparatus. For example, Y type strainers, bucket type strainers, and the like are used.

Reference numeral 3 indicates a pump. Similarly to the strainers, a backup pump may be provided parallelly as the case may be. Reference numeral 4 indicates an upstream side liquid extracting pipe, 5 indicates a downstream side liquid extracting pipe, and 6 is a branch pipe.

The upstream side liquid extracting pipe 4 is a pipe for transferring a liquid under reduced pressure contained in an apparatus under reduced pressure, and has an upstream end opening in the apparatus under reduced pressure though not shown. In the present invention, "upstream end opening in the apparatus under reduced pressure" means that the upstream end of the liquid extracting pipe opens in a chamber, column and the like in which liquid under reduced pressure is contained. The apparatus under reduced pressure includes, for example, a vacuum distillation apparatus, specifically the apparatus shown in FIG. 2 or FIG. 4. Substances handled in such an apparatus include, for example, easily polymerizable substances selected from the group consisting of acrylic acid, methacrylic acid, and esters thereof.

A valve a and a valve b are provided upstream and downstream of the strainer 1, respectively, and the strainer 1 is also provided with an exhaust valve h. Also, a valve c and a valve d are provided upstream and downstream of the strainer 2, respectively, and the strainer 2 is also provided with an exhaust valve i.

The exhaust valves h and i are used for expelling and discharging air in a part sandwiched between valves a and b, or c and d, by liquid discharged from the pump 3 and fed through the branch pipe 6; therefore, the exhaust valves h and i are provided at a highest position between the part sandwiched between the valves a and b, or c and d.

Note that in FIG. 1, the branch pipe 6 opens between the strainer 1 and the valve a. However, it may open between the strainer 1 and the valve b. The same is true for the strainer 2; the branch pipe 6 may be opened on a downstream side of the strainer 2.

Action of the liquid extraction apparatus is described as follows. When the strainer 1 is in action, all the valves are closed except for the valves a and b that are open. Upon switching from the strainer 1 to the strainer 2, valves i and g are opened, and then valve e is slowly opened to allow the liquid discharged from the pump to flow into the strainer 2 through the branch pipe 6. Inclusive of the strainer 2, air in the part sandwiched between valves c and d is discharged form the exhaust valve i by being pushed by a discharge liquid.

When the part sandwiched between valves c and d is completely replaced by the discharge liquid, valves e, g and i are closed, and valves c and d are opened to bring the strainer 2 into action. Then, valves a and b are closed and the strainer 1 is separated from the line. Subsequently, valves j and h are opened to draw out liquid from within the strainer 1. Thereafter, the strainer 1 is opened and an interior thereof is cleared to obtain a backup strainer. It is preferable that liquid inside the branch pipe 6 is drawn out by opening valve k.

<A Process for Producing an Easily Polymerizable Substance According to the Present Invention>

Hereinafter, a process for producing an easily polymerizable substance according to the present invention will be described in detail.

The present invention is a process for producing an easily polymerizable substance using a treating apparatus including: one or two, or more, treating columns for handling an easily polymerizable substance; a pump provided for each treating column for transferring an outlet liquid from the treating column; and two or more strainers parallelly installed in a liquid extraction pipe extending from the treating column to the pump, wherein: in each treating column, one each of the two or more strainers is used, a time for switching the strainers is determined by measuring a difference between pressure on an upstream side of one strainer of the liquid extraction pipe used on the strainer side, and pressure on a downstream side of the strainer of the liquid extraction pipe, and the one strainer is switched to another strainer out of the two or more strainers.

Examples of typical easily polymerizable substances include acrylic acid, methacrylic acid, and esters thereof. Examples of the acrylates include methyl acrylate, ethyl acrylate, butyl acrylate, isobutyl acrylate, tertiarybutyl acrylate, 2-ethylhexyl acrylate, 2-hydroxyethyl acrylate, 2-hydroxypropyl acrylate, and methoxtethyl acrylate. Examples of the methacrylates include methyl methacrylate, butyl methacrylate, isobutyl methacrylate, tertiarybutyl methacrylate, and 2-hydroxyethyl methacrylate.

In the treating apparatus used in the present invention, the treating column for handling an easily polymerizable substance includes any one of, or combinations of, a distillation column, an evaporation column, a reflux tank, an extraction column, an absorption column, a high boiling point decomposition reactor, an esterification reactor, and a heat exchanger. In a case of combinations of two or more of these components, each apparatus that constitutes the treating column is provided with a pump for transferring an outlet liquid, and two or more strainers parallelly installed in a liquid extraction pipe of the pump extending from the treating column.

The pump employed in the present invention is used for transferring an outlet liquid from the treating column to a subsequent appliance, and specific examples thereof include a general reciprocating pump, a rotary pump, a volute pump, an axial flow pump, and a mixed flow pump as well as a specialty pump such as a jet pump and the like.

In addition, the subsequent appliance includes the aforementioned treating columns for handling easily polymerizable substances in the present invention, such as any one of, or combinations of, a distillation column, an evaporation column, a reflux tank, an extraction column, an absorption column, a high boiling point decomposition reactor, an esterification reactor, and a heat exchanger as well as tanks, waste water disposing appliance, incinerators and the like.

FIG. 2 shows one example of an appliance that constitutes the treating apparatus for handling the easily polymerizable substances. Specifically, the treating apparatus including a distillation column for producing acrylic acid, methacrylic acid, and esters thereof as a treating column is shown.

The treating apparatus shown in FIG. 2 includes distillation columns installed in series or parallel, a pump for transferring an outlet liquid from each distillation column, and two or more strainers parallelly installed in a liquid extraction pipe connecting each distillation column and the pump (provided that in FIG. 2, one distillation column and one pump are illustrated).

In some cases, an evaporation column, an extraction column and the like may be installed as necessary between the distillation columns, and each of these is installed with a pump for transferring outlet liquid and two or more strainers parallelly installed in the liquid extraction pipe connecting the distillation column and the pump.

Liquid fed from an introduction line 7 to a distillation column 8 is distilled. Distilled gas is transferred from an outlet at a top of the column to a condenser 9 where the gas is cooled. Then a liquid is transferred to a reflux tank 10. A portion of the liquid in the reflux tank 10 is returned to the distillation column 8 via a liquid extraction pipe 11 for transferring outlet liquid from the reflux tank 10 and pump 12 through a reflux line 13. A remainder is extracted from a column top extraction line 14 and transferred to a subsequent appliance.

Spent gas is transferred to a spent condenser 16 through a bent line 15 to be cooled, and after valuable substances in the gas are recovered, the spent gas is introduced into a vacuum appliance 17 as the case may be. Depending on operational conditions of the treating apparatus, the vacuum appliance 17 is unnecessary.

Here, the valuable substances indicate organic substances handled in the distilling column 8. For example, when manufacturing acrylic acid, valuable substances include acrylic acid, the solvents used when manufacturing acrylic acid (such as methyl ethyl ketone, methyl isobutyl ketone, toluene, and isopropyl acetate). When manufacturing acrylates, the valuable substances include methyl acrylate, ethyl acrylate, butyl acrylate, isobutyl acrylate, tertiarybutyl acrylate, 2-ethylhexyl acrylate, 2-hydroxyethyl acrylate, 2-hydroxypropyl acrylate, and methoxyethyl acrylate and the like; methanol, ethanol, 2-ethylhexanol, methoxyethanol and the like as raw materials; and benzene, toluene and the like as a solvent.

A condensate and non-condensed gas are discharged from the vacuum appliance 17 through an exhaust line 18. Since a small amount of valuable substances are contained in the exhaust line 18, the condensate and the non-condensed gas are recycled to a production process for acrylic acid, methacrylic acid, and esters thereof, as the case may be.

To transfer a column bottom liquid (outlet liquid) of the distillation column 8 to a subsequent appliance, the outlet liquid is extracted through a liquid extraction pipe 19, pump 20 and column bottom extraction line 21. A portion of the column bottom liquid is returned to the distillation column 8 via a reboiler 23 through a reboiler circulation line 22.

Since FIG. 2 is a schematic drawing, a polymerization inhibitor liquid extraction pipe, and an air liquid extraction pipe that are necessary depending on conditions of the system in distillation of acrylic acid, methacrylic acid, and esters thereof are omitted.

Referring to FIG. 3, explanation will be made of a monitoring system for conditions of two or more strainers parallelly installed in a liquid extraction pipe extending from a pump for transferring outlet liquid of a treating column from the treating column to a subsequent appliance.

The aforementioned strainers are parallelly installed for the treating columns and corresponding pumps in a number of two or more for one pump in the liquid extraction pipe. During operation, the strainers are used one by one. The present invention is characterized by determining a time of switching the strainers to measure a difference between pressure on the upstream side of a strainer being used of the liquid extraction pipe and pressure on a downstream side of the strainer being used of the liquid extraction pipe, and switching the strainer to another strainer.

The number of strainers installed for one pump is not particularly limited; usually three or less, preferably two. The number of strainers being four or more is not cost effective since the number of strainers that do not participate in an operation is increased. Note that a size of the strainers may be the same or different.

Liquid is fed from a treating column (in FIG. 2, the distillation column 8, reflux tank 10, and the like) via a liquid extraction pipe 24 to the pump 3. In FIG. 3, two strainers, the strainers 1 and 2, are installed parallelly with respect to the pump 3 and the strainer 1 is used and the strainer 2 is a backup with valves a, b, l, and o being open and other valves being closed.

A difference between pressure of liquid extraction pipe 24, that is pressure of an upstream side of the strainer (a pressure detection part 25 of the liquid extraction pipe), and pressure of the liquid extraction pipe 26, that is the pressure of the downstream side of the strainer (a pressure detection part 27 of the liquid extraction pipe) is observed on a differential pressure gauge 28. This observed information is transmitted to an instrument room installed in the treating apparatus. In a case where entrapment of polymerisate is in small amounts, it is sufficient that this differential pressure can be observed in situ. In FIG. 2, as a cable for transmitting signals from a detection terminal as observed information, pressure information transmission lines 29 and 30 are installed.

As polymerisate is accumulated in the strainer 1, the difference between the pressure of the liquid extraction pipe 24 (the pressure detection part 25 of the liquid extraction pipe) and the pressure of the liquid extraction pipe 26 (the pressure detection part 27 of the liquid extraction pipe) is increased. Judgment of a time of switching when the difference comes to be increased depends on a condition of the system (capability of the pump, composition of liquid in each line, diameter of the pipe in each line, and the like) and hence is not limited. Generally, 1.5 to 150 times, preferably 1.5 to 100 times, more preferably 1.5 to 50 times based on the differential pressure in a state where no polymerisate is present (initial stage of operation of the strainer).

The strainers used in the treating apparatus in the present invention are not particularly limited in terms of their type; any one of those used in general chemical plants may be used. Specific examples thereof include Y type strainers, bucket type strainers, T type strainers, and the like.

A format and a differential pressure gauge for detection of pressures for measuring a differential pressure of the strainers in the present invention are not particularly limited, and any of those used in general chemical plants may be employed. Specifically, examples of a pressure detector include a diaphragm type pressure gauge. Examples of the differential pressure gauge include a diaphragm displacement type electronic pressure difference transmitter (generally referred to as a capillary type). For example, EDR-7 manufactured by Hitachi Ltd. corresponds to this.

A position of installing extraction nozzles (31 and 32 in FIG. 3) for connecting a pressure detection end to a liquid extraction pipe for measuring a differential pressure of the strainer in the present invention is preferably in an upper part of the liquid extraction pipe of the strainer being used (liquid extraction pipes 24 and 26 in FIG. 3). Although detection is possible even when the nozzles are installed at the same horizontal position as the liquid extraction pipes 24 and 26, or in a lower part of the liquid extraction pipes, influence of liquid flow in the liquid extraction pipe is likely, so that installing in an upper part of the liquid extraction pipes is optimal. An angle of installment of the nozzles with respect to the liquid extraction pipe is preferably 5 to 175°, more preferably 70 to 110°, in the upper part of the liquid extraction pipes. An optimal angle is 90°.

Generally, extraction nozzles for connecting the pressure detection end and the liquid extraction pipe are installed. A length of each extraction nozzle is within 800 mm, and within preferably 500 mm in terms of horizontal piping. A long extraction nozzle may generate polymerisate due to stagnation of liquid. The extraction nozzle that connects the liquid extraction pipe and the pressure detection end may be installed with a valve which can open and close. An infimum of distance is not limited since the pressure detector may be installed directly in the liquid extraction pipe depending on a kind of the pressure detector.

<An Apparatus and a Method for Handling an Easily Polymerizable Substance of the Present Invention>

An apparatus for handling an easily polymerizable substance of the present invention comprises: a decompressor for handling the easily polymerizable substance under reduced pressure; a liquid extraction pipe having an upstream end that opens in the decompressor; a pump provided in a middle of the liquid extraction pipe; a plurality of strainers connected parallel to one another, to the liquid extraction pipe on an upstream side of the pump; and valves provided on an upstream side and downstream side of each of the strainers, and comprises at least one of constructions (A) and (B) below:

(A) an exhaust device for exhausting air in a part sandwiched between the valves provided on the upstream side and downstream side of each strainer, and a branch pipe that connects the part sandwiched between the valves provided on the upstream side and downstream side of each strainer and the liquid extraction pipe on the downstream side of the pump; and (B) a device for measuring a differential pressure between a pressure in the liquid extraction pipe on the upstream side of each strainer and a pressure in the liquid extraction pipe on the downstream side of each strainer.

The apparatus for handling the easily polymerizable substance of the present invention may have only construction (A) or only construction (B) out of the aforementioned constructions (A) and (B), or both constructions (A) and (B).

In a case where the apparatus has only construction (A) out of constructions (A) and (B), the apparatus for handling the easily polymerizable substance of the present invention can avoid occurrence of disturbance in operation caused by air contained in a backup strainer.

In a case where the apparatus has only construction (B) out of constructions (A) and (B), the apparatus for handling the easily polymerizable substance of the present invention can switch the two or more strainers parallelly installed in the liquid extraction pipe connecting the pump for transferring an outlet liquid of the treating column and the treating column for handling the easily polymerizable substance at proper times.

In a case where the apparatus has both constructions (A) and (B) out of the above-mentioned constructions (A) and (B), it becomes possible to avoid problems of operation caused by air contained in a backup strainer, and to switch two or more strainers parallelly installed in the liquid extracting pipe for transferring the outlet liquid of the treating column from the treating column for handling an easily polymerizable substance to the pump for transferring the outlet liquid of the treating column at proper times.

The aforementioned decompressor may be constructed by an apparatus for handling an easily polymerizable substance and an apparatus for forming an atmosphere under reduced pressure. As such a decompressor, for example, an apparatus for distilling an easily polymerizable substance selected from the group consisting of acrylic acid, methacrylic acid, and esters thereof under reduced pressure may be mentioned. As the apparatus for handling the easily polymerizable substance may be used the aforementioned treating apparatus. As the apparatus for forming an atmosphere under reduced pressure, a well-known vacuum appliance such as a vacuum pump may be used.

Note that construction of the aforementioned decompressor is not limited to one that has an apparatus for forming atmosphere under reduced pressure, but may be an apparatus for handling an easily polymerizable substance in an atmosphere under reduced pressure. Such apparatus includes, for example, the aforementioned treating column such as a heat exchanger, and the like, connected to a vacuum pump.

An outlet liquid of the aforementioned decompressor is a liquid extracted from the decompressor. Examples of such a liquid include column bottom liquid of the distillation column and condensate of a gas component obtained by distillation and so forth.

The upstream end of the aforementioned liquid extraction pipe is open in the decompressor. This means that the upstream end of the liquid extraction pipe is open in a chamber or a column formed so as to be under a reduced pressure atmosphere.

The aforementioned exhaust device may be a device that forcibly discharges air in the system such as a vacuum appliance, e.g., a vacuum pump. It is preferable from a view point of simplification of construction of the apparatus to configure, that a liquid introduced from the aforementioned branch pipe to the part sandwiched between the valves installed on an upstream side and downstream side of each strainer will expel air in this part.

For the aforementioned device for measuring the differential pressure, a well-known device that can measure pressure of a liquid in a pipe may be used similarly to a differential pressure gauge used in the treating apparatus employed in the method for producing the easily polymerizable substance of the present invention.

Further, the aforementioned device for measuring differential pressure is preferably one that is installed by using the aforementioned extraction nozzles. Also, in the present invention, the aforementioned device for measuring the differential pressure is preferably provided such that the differential pressure measured can be transmitted to an instrument room, for the aforementioned decompressor, for continuously measuring the differential pressure of the aforementioned strainers.

The apparatus for handling an easily polymerizable substance of the present invention may be specifically configured by applying the apparatus shown in FIG. 1 to the apparatus shown in FIG. 2 or FIG. 4, or applying the apparatus shown in FIG. 3 to the apparatus shown in FIG. 2 or FIG. 4.

A method for handling an easily polymerizable substance of the present invention is a method for handling an easily polymerizable substance using the apparatus for handling an easily polymerizable substance of the present invention, and comprises: using a plurality of strainers one by one; determining times for switching the strainers to measure a difference between a pressure in a liquid extraction pipe on an upstream side of the strainer being used and a pressure in the liquid extraction pipe on a downstream side of the strainer being used; and switching the strainer being used to another strainer out of the plurality of strainers.

According to this method, two or more strainers parallelly installed in the liquid extraction pipe connecting the pump, for transferring an outlet liquid of a treating column and the treating column for handling the easily polymerizable substance, can be switched at proper times.

Further, when the method for handling an easily polymerizable substance of the present invention further includes: discharging air in a part sandwiched between valves provided on an upstream side and downstream side of the another strainer; feeding a discharge liquid of the pump from the branch pipe to the part, and switching the strainer being used to another strainer after replacing air in the part with the discharge liquid, it also becomes possible to avoid problems of operation caused by air contained in a backup strainer.

Note that, in the invention, "handling" an easily polymerizable substance means various operations related to a liquid containing an easily polymerizable substance such as production of an easily polymerizable substance, separation of an easily polymerizable substance, washing of an easily polymerizable substance, purification of an easily polymerizable substance, and transportation of an easily polymerizable substance.

DETAILED DESCRIPTION OF THE PREFERRED EMBODIMENTS

Hereinafter, the present invention will be described in more detail by examples and comparative examples. However, the present invention is not limited to the following examples unless going beyond the gist of the present invention.

EXAMPLE 1

Explanation will be made of a case where the liquid extraction apparatus according to the present invention was applied to the vacuum distillation apparatus shown in FIG. 4, and purifies acrylic acid to form high purity acrylic acid.

Figure 1:
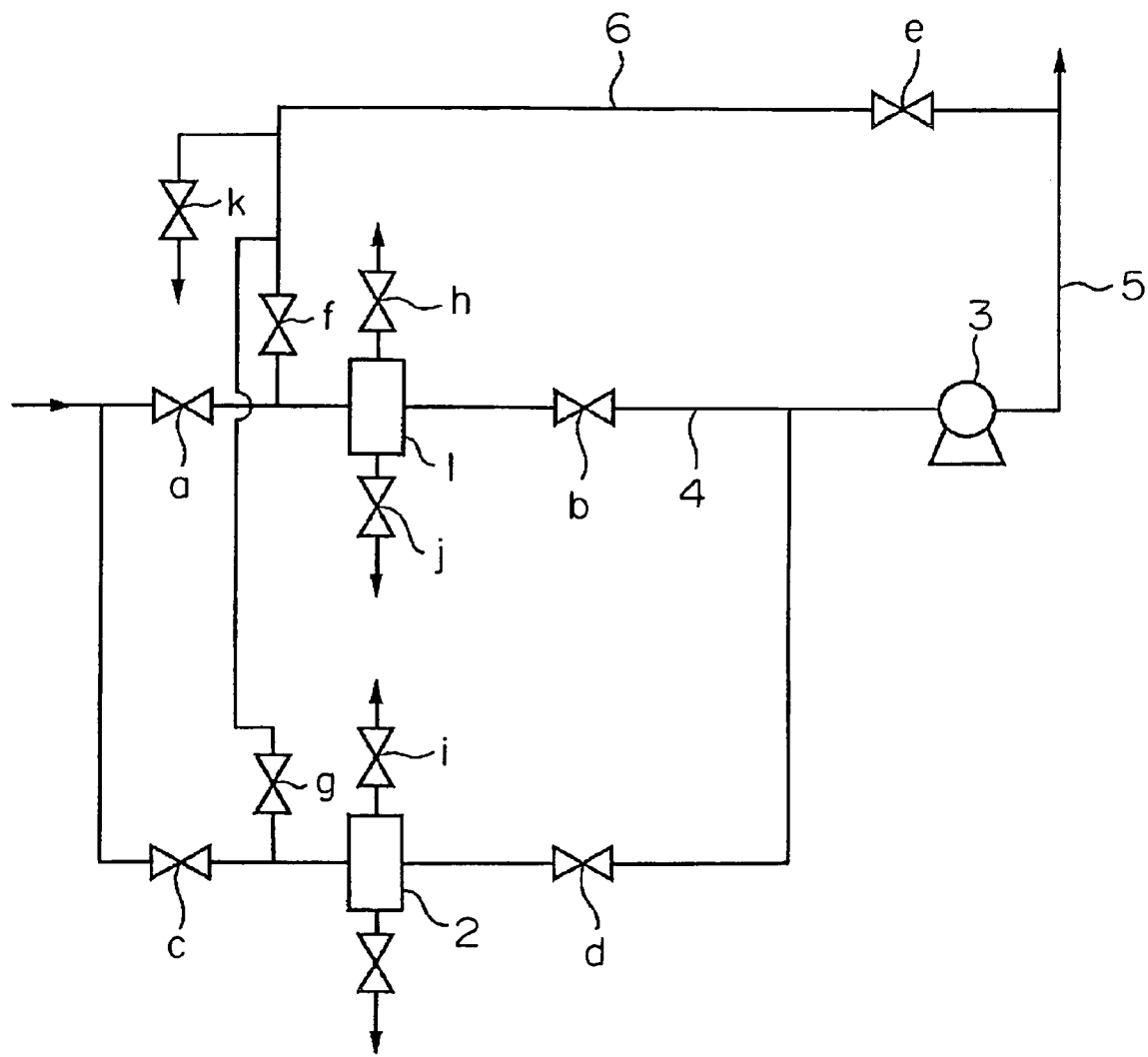
FIG. 1 is a diagram showing one example of an apparatus for extracting a liquid according to the present invention.
Figure 4:
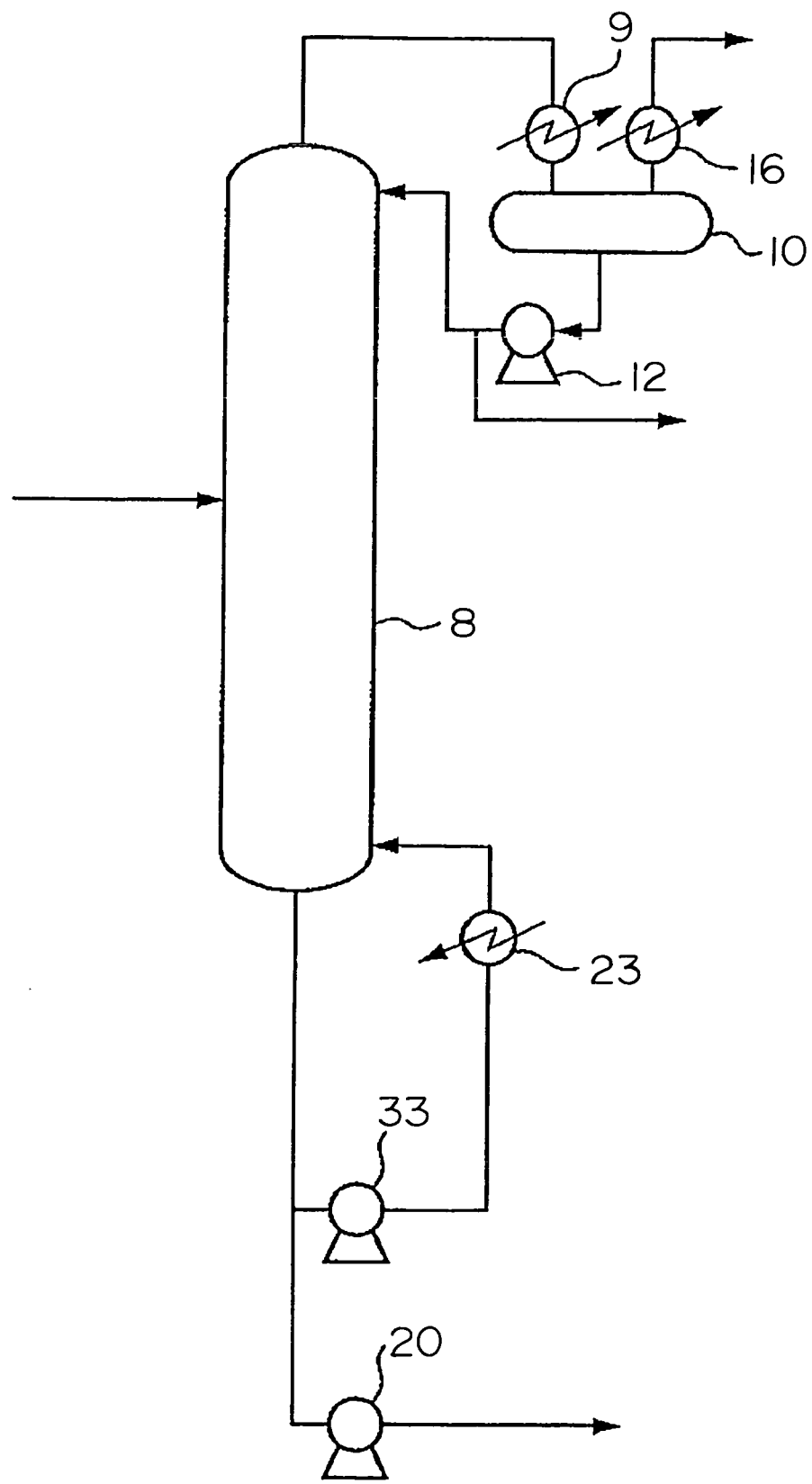
FIG. 4 shows one example of a vacuum distillation column to which an apparatus for extracting a liquid according to the present invention is applied.

In FIG. 4, reference numeral 8 stands for a distillation column, 23 stands for a reboiler, 33 stands for a reboiler feed pump, 10 stands for a reflux tank, 12 stands for a pump for extracting a condensate, 20 stands for a pump for extracting a column bottom liquid, and 9 and 16 stand for condensers. At a top and bottom of the column 8 are attached the liquid extraction apparatus shown in FIG. 1, each having a pump 12 and a pump 20. Both strainers 1 and 2 are basket type strainers. Note that in FIG. 4, a polymerization inhibitor feeding apparatus, a vacuum generating appliance, and other ancillary appliance are omitted.

The aforementioned vacuum distillation apparatus was operated with the distillation column being at a column top pressure of 3 kPa and a column bottom pressure of 11 kPa. During this operation, switching from the strainer 1 to the strainer 2 at the column top and the column bottom of the liquid extraction apparatus performed in the aforementioned method caused neither change in an operation of the pump nor change in differential pressure between the column bottom and the column top.

After 3 months, the strainer 2 of the liquid extraction apparatus at the column top and the column bottom was switched to the strainer 1 again in the aforementioned method. Checking an interior of the strainer 2 indicated no polymerisate.

COMPARATIVE EXAMPLE 1

In contrast, switching from strainer 1 to strainer 2 of the column top and the column bottom of the liquid extraction apparatus was performed by a method in which valves c and d were slowly opened while other valves remained closed. Then, both pumps generated abnormal sounds and pressure of the distillation column abruptly varied. This is considered because air in the part sandwiched by valves c and d including the strainer 2 flowed into the distillation column via the pump, or flowed backward.

After a while, the abnormal sounds of the pump disappeared and valves a and b were closed, thus completing switching of the strainers. Subsequently, continued operation of the distillation column led to a gradual increase in differential pressure between the column bottom and the column top.

Then, the strainer 2 of the liquid extraction apparatus at the column top and the column bottom was switched again to the strainer 1. Checking an interior of each strainer 2 indicated polymerisate.

EXAMPLE 2

Figure 2:
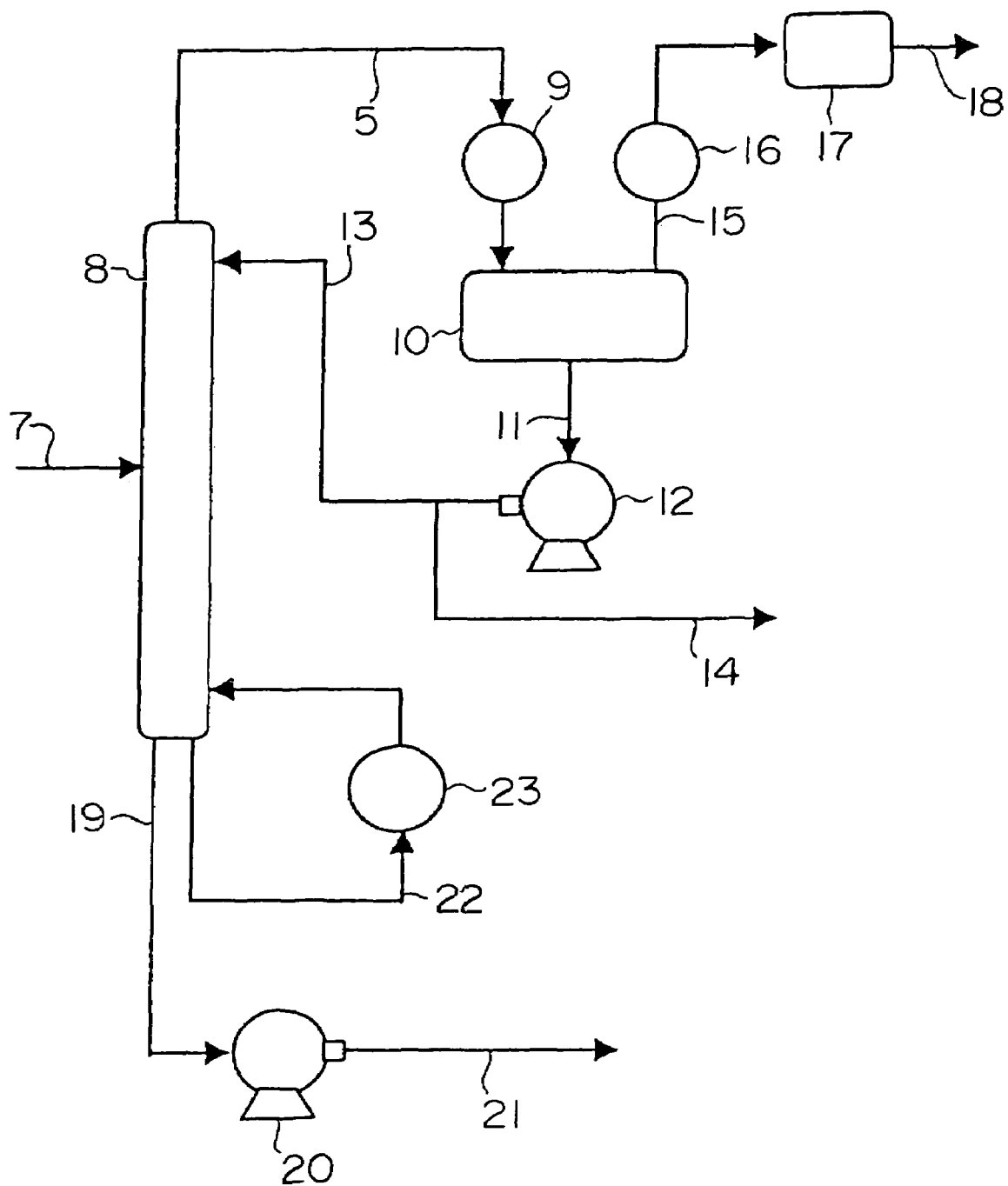
FIG. 2 is a diagram showing one embodiment of a treating apparatus used in a process for producing an easily polymerizable substance of the present invention.

By using the treating apparatus with the distillation column 8 as shown in FIG. 2, acrylic acid was purified.

Figure 3:
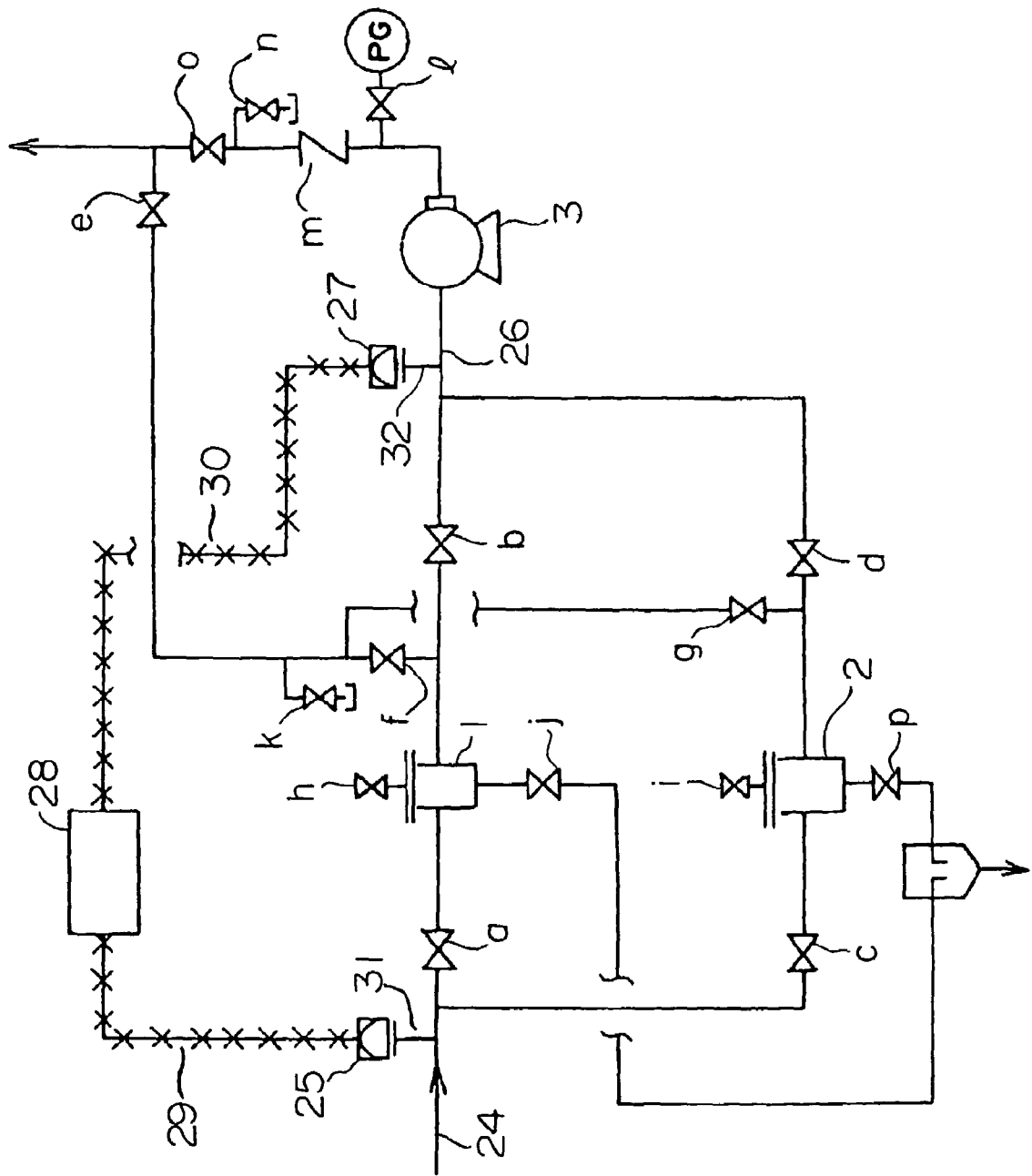
FIG. 3 is a schematic diagram showing a pump and its surroundings of a treating apparatus used in the present invention.

The distillation column 8 had a column top pressure at 3 kPa and a column bottom pressure of 11 kPa, and a differential pressure of strainers installed in a liquid extraction pipe of a pump for transferring an outlet liquid from the column bottom was continuously measured. Note that a condition of the surroundings of the pump was the same as that shown in FIG. 3 except that in this example, two backup strainers were provided. Extraction nozzles (31 and 32) for connecting a pressure detection end of a differential pressure gauge to liquid extraction pipes 24 and 26 were installed at 90° to the liquid extraction pipe and had a length of 150 mm.

A differential pressure at an initial stage of operation of the strainer was 1.6 kPa. After continuous operation, the differential pressure was increased slowly and reached 19 kPa after 35 days. Then, the strainer was switched and an interior thereof was checked. Then, polymerisate was confirmed.

Operation of the distillation column was continued, and after 30 days, the differential pressure became 20 kPa so that the strainer was further switched and an interior thereof was checked. Polymerisate was confirmed in this strainer. Operation of the distillation column could be continued further.

As described above, a time of switching the strainers could be well judged.

COMPARATIVE EXAMPLE 2

By using the same treating apparatus as that in Example 2, except that the apparatus had no differential pressure gauge, as the treating apparatus, an operation was performed. After 42 days, the pump generated cavitation so that a strainer was switched urgently. An interior of the strainer was full of polymerisate.

Cavitation resulted in malfunction of the operation of the distillation column, and after 3 days, cavitation of the pump occurred again. An interior of the strainer was full of polymerisate.

Again, an operation was performed after switching the strainer. The next day, cavitation of the pump occurred again.

Thereafter, an operation with switching of the strainer after occurrence of cavitation resulted in a shorter interval of occurrence of cavitation, and finally the operation became impossible.

The operation of the distillation column was stopped and an interior of the distillation column was checked. As a result, a large amount of polymerisate was confirmed.

INDUSTRIAL APPLICABILITY

Use of an apparatus for extracting a liquid according to the present invention enables extraction of distillation residue at a column bottom and a condensate from a reflux tank at a column top from, for example, a vacuum distillation apparatus for a polymerizable substance without any problems caused to operation of the vacuum distillation apparatus.

Further, according to the present invention, by measuring a differential pressure between pressure on an upstream side of a strainer and pressure on a downstream side of the strainer installed in a top of a liquid extraction pipe connecting a treating column, used for the treating apparatus for handling an easily polymerizable substance, and a pump, and determining times of switching strainers, cavitation of the pump during operation can be avoided, thereby preventing variation in operation of the pump or an appliance connected before and after the pump, and providing a process for efficiently producing an easily polymerizable substance.

Further, according to the apparatus and the method for handling an easily polymerizable substance of the present invention, in handling of the easily polymerizable substance, problems of operation caused by air contained in a backup strainer can be avoided; two or more strainers parallelly installed in a liquid extracting pipe for transferring an outlet liquid of the treating column from a treating column for handling an easily polymerizable substance to a pump for transferring the outlet liquid of the treating column can be switched at proper times; or the aforementioned problems in the operation can be avoided and the aforementioned strainers can be switched at proper times.

The invention claimed is:

1. An apparatus for handling an easily polymerizable substance, comprising:
   a decompressor for handling under reduced pressure a liquid containing the easily polymerizable substance;
   a liquid extraction pipe for extracting the liquid from said decompressor, said liquid extraction pipe having an upstream end that opens in said decompressor;
   a pump in a mid-section of said liquid extraction pipe;
   a first strainer connected to said liquid extraction pipe on an upstream side of said pump;
   a second strainer connected to said liquid extraction pipe on the upstream side of said pump, said second strainer being in parallel with said first strainer;
   a first valve on an upstream side of said first strainer;
   a second valve on a downstream side of said first strainer;
   a third valve on a upstream side of said second strainer;
   a fourth valve on a downstream side of said second strainer;
   a first exhaust device for exhausting air from a part between said first valve and said second valve;
   a second exhaust device for exhausting air from a part between said third valve and said fourth valve; and
   a branch pipe connecting said part between said first and second valves and said part between said third and fourth valves with a part of said liquid extraction pipe on a downstream side of said pump,
   wherein said decompressor comprises a device for distilling under reduced pressure an easily polymerizable polymer selected from the group consisting of acrylic acid, methacrylic acid, and esters thereof.

2. The apparatus according to claim 1, wherein
   said first exhaust device is for exhausting air from said part between said first and second valves in response to the liquid when introduced from said branch pipe to said part between said first and second valves and expelling the air from said part between said first and second valves, and said second exhaust device is for exhausting air from said part between said third and fourth valves in response to the liquid when introduced from said branch pipe to said part between said third and fourth valves and expelling the air from said part between said third and fourth valves.

3. The apparatus according to claims 2, further comprising:
a device for measuring a difference between a pressure in said liquid extraction pipe on an upstream side of said first and second strainers and a pressure in said liquid extraction pipe on an a downstream side of said first and second strainers.

4. The apparatus according to claim 1, further comprising:
a device for measuring a difference between a pressure in said liquid extraction pipe on an upstream side of said first and second strainers and a pressure in said liquid extraction pipe on an a downstream side of said first and second strainers.

5. An apparatus for extracting a liquid from a device under reduced pressure, comprising:
a liquid extraction pipe for transferring a liquid under reduced pressure from a device under reduced pressure, said liquid extraction pipe having an upstream end that opens in the device;
a pump in a mid-section of said liquid extraction pipe;
a first strainer connected to said liquid extraction pipe on an upstream side of said pump;
a second strainer connected to said liquid extraction pump on the upstream side of said pump, said second strainer being in parallel with said first strainer;
a first valve on an upstream side of said first strainer;
a second valve on a downstream side of said first strainer;
a third valve on a upstream side of said second strainer;
a fourth valve on a downstream side of said second strainer;
a first exhaust device for exhausting air from a part between said first valve and said second valve;
a second exhaust device for exhausting air from a part between said third valve and said fourth valve; and
a branch pipe connecting said part between said first and second valves and said part between said third and fourth valves with a part of said liquid extraction pipe on a downstream side of said pumps,
wherein the device comprises a vacuum distillation apparatus for an easily polymerizable polymer selected from the group consisting of acrylic acid, methacrylic acid, and esters thereof.

6. The apparatus according to claim 5, wherein
said first exhaust device is for exhausting air from said part between said first and second valves in response to the liquid when introduced from said branch pipe to said part between said first and second valves and expelling the air from said part between said first and second valves, and
said second exhaust device is for exhausting air from said part between said third and fourth valves in response to the liquid when introduced from said branch pipe to said part between said third and fourth valves and expelling the air from said part between said third and fourth valves.

* * * * *